(12) United States Patent
Bowman et al.

(10) Patent No.: US 12,185,989 B2
(45) Date of Patent: Jan. 7, 2025

(54) FOAMING AGENTS AND COMPOSITIONS CONTAINING FLUORINE SUBSTITUTED OLEFINS, AND METHODS OF FOAMING

(71) Applicant: HONEYWELL INTERNATIONAL INC., Morris Plains, NJ (US)

(72) Inventors: James M. Bowman, Geneva, IL (US); David J. Williams, East Amherst, NY (US)

(73) Assignee: HONEYWELL INTERNATIONAL INC., Charlotte, NC (US)

(*) Notice: Subject to any disclaimer, the term of this patent is extended or adjusted under 35 U.S.C. 154(b) by 45 days.

(21) Appl. No.: 16/878,799

(22) Filed: May 20, 2020

(65) Prior Publication Data
US 2021/0007784 A1    Jan. 14, 2021

Related U.S. Application Data

(60) Division of application No. 15/893,955, filed on Feb. 12, 2018, now abandoned, which is a division of
(Continued)

(51) Int. Cl.
A61B 17/70      (2006.01)
C08J 9/00       (2006.01)
(Continued)

(52) U.S. Cl.
CPC ...... A61B 17/7071 (2013.01); A61B 17/7026 (2013.01); A61B 17/7043 (2013.01);
(Continued)

(58) Field of Classification Search
CPC ............ A61B 17/7071; A61B 17/7026; A61B 17/7043; A61B 17/7067; C08J 9/0066; C08J 9/122; C08J 9/127; C08J 9/141; C08J 9/142; C08J 9/144; C08J 9/146; C08J 9/149; C08J 9/34; C08J 2201/022;
(Continued)

(56) References Cited

U.S. PATENT DOCUMENTS 2,834,748 A   5/1958   Bailey
2,846,458 A   8/1958   Haluska
(Continued)

FOREIGN PATENT DOCUMENTS

EP   0398147 A2   11/1990
EP   0644173 A1    3/1995
(Continued)

OTHER PUBLICATIONS

Jan H. Schutt, "Polyurethane Foam Industry Prepares for 'Zero ODP'," Plastics Technology—Online article (http://www/plasticstechnology.com/articles/19911 fa3.html) (Jan. 2, 2006) US.
(Continued)

Primary Examiner — Frances Tischler
(74) Attorney, Agent, or Firm — FisherBroyles, LLP; Joseph F. Posillico

(57) ABSTRACT

Various uses of fluoroalkenes, including tetrafluoropropenes, particularly (HFO-1336) in a variety of applications, including as blowing agents for integral skin foams are disclosed.

9 Claims, 1 Drawing Sheet

Related U.S. Application Data application No. 14/209,148, filed on Mar. 13, 2014, now abandoned, which is a continuation-in-part of application No. 11/474,887, filed on Jun. 26, 2006, now Pat. No. 9,796,848.

(60) Provisional application No. 61/801,125, filed on Mar. 15, 2013, provisional application No. 60/784,731, filed on Mar. 21, 2006, provisional application No. 60/693,853, filed on Jun. 24, 2005.

(51) Int. Cl.
    *C08J 9/12* (2006.01)
    *C08J 9/14* (2006.01)
    *C08J 9/34* (2006.01)

(52) U.S. Cl.
    CPC ......... *A61B 17/7067* (2013.01); *C08J 9/0066* (2013.01); *C08J 9/122* (2013.01); *C08J 9/127* (2013.01); *C08J 9/141* (2013.01); *C08J 9/142* (2013.01); *C08J 9/144* (2013.01); *C08J 9/146* (2013.01); *C08J 9/149* (2013.01); *C08J 9/34* (2013.01); *C08J 2201/022* (2013.01); *C08J 2201/03* (2013.01); *C08J 2203/06* (2013.01); *C08J 2203/12* (2013.01); *C08J 2203/14* (2013.01); *C08J 2203/142* (2013.01); *C08J 2203/162* (2013.01); *C08J 2203/182* (2013.01); *C08J 2205/052* (2013.01); *C08J 2325/06* (2013.01); *C08J 2375/04* (2013.01)

(58) Field of Classification Search
    CPC .............. C08J 2201/03; C08J 2203/06; C08J 2203/12; C08J 2203/14; C08J 2203/142; C08J 2203/162; C08J 2203/182; C08J 2205/052; C08J 2325/06; C08J 2375/04; A61K 8/602; A61K 8/9789; A61Q 19/02
    See application file for complete search history.

(56) References Cited

U.S. PATENT DOCUMENTS

| | | | |
|---|---|---|---|
| 2,889,379 | A | 6/1959 | Ruh |
| 2,917,480 | A | 12/1959 | Bailey |
| 2,931,840 | A | 4/1960 | Maley |
| 2,996,555 | A | 8/1961 | Rausch |
| 3,085,918 | A | 4/1963 | Sherliker |
| 3,694,530 | A * | 9/1972 | Wolfe ................ C08J 9/34 428/218 |
| 3,723,318 | A | 3/1973 | Butler |
| 3,884,828 | A | 5/1975 | Butler |
| 3,931,381 | A * | 1/1976 | Lindberg ............. B29C 33/60 264/129 |
| 4,465,786 | A | 8/1984 | Zimmer |
| 4,788,352 | A | 11/1988 | Smutny |
| 4,798,818 | A | 1/1989 | Baizer |
| 4,944,890 | A | 7/1990 | Deeb |
| 4,945,119 | A | 7/1990 | Smits |
| 4,994,890 | A | 2/1991 | Caldwell |
| 5,174,083 | A | 12/1992 | Mussell |
| 5,250,208 | A | 10/1993 | Merchant |
| 5,264,461 | A | 11/1993 | Krueger |
| 5,283,003 | A | 2/1994 | Chen |
| 5,362,436 | A * | 11/1994 | Wagner ................ B29C 51/14 428/318.6 |
| 5,520,208 | A | 5/1996 | Schneider |
| 5,532,419 | A | 7/1996 | Van Der Puy |
| 5,578,137 | A | 11/1996 | Shealy |
| 5,616,275 | A | 4/1997 | Chisolm |
| 5,674,451 | A | 10/1997 | Nimitz |
| 5,679,875 | A | 10/1997 | Aoyama |
| 5,710,352 | A | 1/1998 | Tung |
| 5,714,083 | A | 2/1998 | Turner |
| 5,736,063 | A | 4/1998 | Richard |
| 5,744,052 | A | 4/1998 | Bivens |
| 5,788,886 | A | 8/1998 | Minor |
| 5,889,068 | A | 3/1999 | Madaj |
| 5,902,912 | A | 5/1999 | Tung |
| 5,942,149 | A | 8/1999 | Weber, III |
| 5,997,761 | A | 12/1999 | Kaneko |
| 6,041,621 | A | 3/2000 | Olszewski |
| 6,076,372 | A | 6/2000 | Acharya |
| 6,111,150 | A | 8/2000 | Sakyu |
| 6,124,510 | A | 9/2000 | Elsheikh |
| 6,176,102 | B1 | 1/2001 | Novak |
| 6,258,292 | B1 | 7/2001 | Turner |
| 6,274,779 | B1 | 8/2001 | Merkel |
| 6,300,378 | B1 | 10/2001 | Tapscott |
| 6,327,866 | B1 | 12/2001 | Novak |
| 6,374,629 | B1 | 4/2002 | Oberle |
| 6,516,837 | B2 | 2/2003 | Thomas |
| 6,574,973 | B1 | 6/2003 | Desmarteau |
| 6,849,194 | B2 | 2/2005 | Robin |
| 6,858,571 | B2 | 2/2005 | Pham |
| 6,972,271 | B2 | 12/2005 | Thomas |
| 7,230,146 | B2 | 6/2007 | Merkel |
| 7,248,809 | B2 | 7/2007 | Kim |
| 7,279,451 | B2 | 10/2007 | Singh |
| 7,534,366 | B2 | 5/2009 | Singh |
| 2003/0127115 | A1 | 7/2003 | Thomas |
| 2004/0089839 | A1 | 5/2004 | Thomas |
| 2004/0119047 | A1 | 6/2004 | Singh |
| 2004/0127383 | A1 | 7/2004 | Pham |
| 2004/0256594 | A1 | 12/2004 | Singh |
| 2005/0054741 | A1 | 3/2005 | Zipfel |
| 2005/0082510 | A1 | 4/2005 | Ponder |
| 2005/0105947 | A1 | 5/2005 | Kim |
| 2005/0107246 | A1 | 5/2005 | Thomas |
| 2005/0133756 | A1 | 6/2005 | Ponder |
| 2006/0243944 | A1 | 11/2006 | Minor |
| 2008/0230738 | A1 | 9/2008 | Minor |
| 2012/0202904 | A1 * | 8/2012 | Chen ................ C08J 9/149 521/131 |

FOREIGN PATENT DOCUMENTS

| | | | |
|---|---|---|---|
| EP | 1055439 A2 | 11/2000 | |
| EP | 1191080 A2 | 3/2002 | |
| EP | 0974571 B1 | 4/2003 | |
| GB | 950876 A | 2/1964 | |
| JP | 05-179043 B2 * | 7/1993 | ........ C10M 169/041 |
| JP | 5179043 A | 7/1993 | |
| JP | 2004110388 A | 4/2004 | |
| RU | 2073058 C1 | 2/1997 | |
| WO | 03064508 A2 | 8/2003 | |
| WO | 2004037752 A2 | 5/2004 | |
| WO | 2004037913 A2 | 5/2004 | |
| WO | 200510594 A1 | 2/2005 | |
| WO | 2005103187 A1 | 11/2005 | |
| WO | 2005103188 A1 | 11/2005 | |
| WO | 2005105947 A2 | 11/2005 | |

OTHER PUBLICATIONS

Perry Romanowski, "Polyurethane," Gale Edit-How Plastics are Made-Volumes-Polyurethane, http://www.gale-edit.com/products/volumes/polyurethane.htm (Jan. 220067) US.

Downing, Ralph C., "Fluorcarbon Refrigerants Handbook," Prentice Hall, Chapter 3 (1988) pp. 17-34.

Atkinson, W. "Alternate Refrigerant-Scope of Work," SAE Cooperative Research Program, Jul. 26, 2000. US (Exhibit A to Declaration of Rajiv Ratna Singh, dated Apr. 21, 2011).

Rule 132 Declaration of Rajiv Ratna Singh, dated Apr. 21, 2011. US.

XP2343594 Database WPI; Week 199221; Thomson Scientific, London, GB AN 1992-172539; XP2343594, & JP H04 110388 A (Daikin Kogyo KK) 1992-047-10 (English translation consulted).

McIlroy, PhD. et al., "Beneficial Uses of C02. Technologies and Implications For A Carbon Market," Article, Sandia National Labo-

(56) References Cited

OTHER PUBLICATIONS ratories ("C02 as a replacement for HFC-134a refrigerant commonly used in vehicles"). (Undated). US (Exhibit C to Declaration of Rajiv Ratna Singh, dated Apr. 21, 2011).

Society of Automotive Engineers, U.S. Environmental Protection Agency, and the Mobile Air Conditioning Society, The Importance of Motor Vehicle Air Conditioning In Climate Protection, SAE Web site: http://www.sae.org/altrefrigerant/techcenter/alternative-refrig-brochure.pdf (pamphlet), ("Hydrocarbons and transcritical C02 refrigerants are under consideration as a replacement for HFC-134a") (Undated) US (Exhibit B to Declaration of Rajiv Ratna Singh, dated Apr. 21, 2011).

Ashrae Standard, Sealed Glass Tube Method To Test the Chemical Stability of Materials for Use within Refrigerant Systems, ANSI/ASHRAE Standard 97/2007 (supersedes Standard 97-1999), Jun. 2007 U.S.

S.C. Zoz and M.B. Pate, "Critical Solution Temperatures for Ten Different Non-CFC Refrigerants with Fourteen Different Lubricants," International Refrigeration and Air Conditioning Conference, Paper 285, pp. 431-436—(1994) U.S.

"AHRi Low-GWP Alternative Refrigerants Evaluation Program, Public Sector Research," Air Conditioning, Heating and Refrigeration Institute (AHRI), 3 pages (Oct. 15, 2012) U.S.

William L. Kopco, "Beyond CFCs: Extending the Search for New Refrigerants," Article in Proceedings of ASHRAE's 1989 CFC Technology Conference, pp. 39-46, National Institute of Standards and Technology, Gaithersburg, MD. Sep. 27-28, 1989 U.S.

McLinden et al., "Quest for Alternatives—A molecular approach demonstrates tradeoffs and limitations are inevitable in seeking refrigerants," ASHRAE Journal, pp. 32-42, Dec. 1987, U.S.

Takizawa et al., "Flammability assessment of $CH_2=CFCF_3$: Comparison with fluoroalkenes and fluoroalkanes," J. Hazardous Materials, vol. 172, pp. 1329-1338 (2009) U.S.

Kondo, S. et al. Flammability limits of olefinic and saturated fluoro-compounds. Journal of Hazardous Materials, 2009, 171, 613-618 . (Year: 2009).

Saunders and Frisch, "Polyurethanes Chemistry & Technology," vol. XVI, Part I and Part II Technology, John Wiley and Sons, New York, NY (1962) pp. 193 to 201 and 219 to 223. US.

Morrissey, C.J.: Nearly Azeotropic Mixtures to Replace Refrigerant 12. In: National Aeronautics and Space Administration Contract No. NAS 7-918, Aug. 1992, NASA Tech Brief, vol. 16, No. 8 item #122.

Bing Co-Pilot, response to querry: "Can any blowing agent be used to make integral skin foam?", May 7, 2024.

Randall and Lee, "The polyurethanes book," John Wiley & Sons, LTD, Dec. 2012, pp. 339-341.

\* cited by examiner

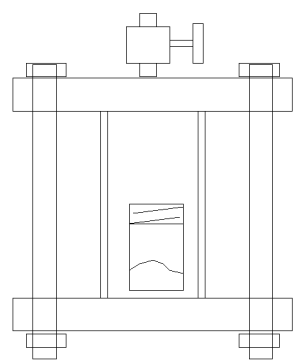

FOAMING AGENTS AND COMPOSITIONS CONTAINING FLUORINE SUBSTITUTED OLEFINS, AND METHODS OF FOAMING

The present application is a division of U.S. application Ser. No. 15/893,955, filed Feb. 12, 2018 (now pending) which is a division of U.S. application Ser. No. 14/209,148, filed Mar. 13, 2014 (now abandoned), which application claims the priority benefit of U.S. Provisional Application No. 61/801,125, filed Mar. 15, 2013, the contents of which are incorporated herein by reference. Application Ser. No. 14/209,148 is also a continuation-in-part of U.S. application Ser. No. 11/474,887, filed Jun. 26, 2006 (now U.S. Pat. No. 9,796,848, issued Oct. 24, 2017), which in turn is related to and claims the priority benefit of U.S. Provisional Application No. 60/784,731, filed Mar. 21, 2006, and U.S. Provisional Application No. 60/693,853, filed Jun. 24, 2005. The disclosure of each of the above is incorporated herein by reference in its entirety.

FIELD OF THE INVENTION

This invention relates to compositions, methods and systems having utility in numerous applications, including particularly heat transfer systems such as refrigeration systems. In preferred aspects, the present invention is directed to refrigerant compositions which comprise at least one multi-fluorinated olefin of the present invention.

BACKGROUND

Fluorocarbon based fluids have found widespread use in many commercial and industrial applications, including as aerosol propellants and as blowing agents. Because of certain suspected environmental problems, including the relatively high global warming potentials, associated with the use of some of the compositions that have heretofore been used in these applications, it has become increasingly desirable to use fluids having low or even zero ozone depletion potential, such as hydrofluorocarbons ("HFCs"). Thus, the use of fluids that do not contain substantial amounts of chlorofluorocarbons ("CFCs") or hydrochlorofluorocarbons ("HCFCs") is desirable. Furthermore, some HFC fluids may have relatively high global warming potentials associated therewith, and it is desirable to use hydrofluorocarbon or other fluorinated fluids having as low global warming potentials as possible while maintaining the desired performance in use properties. Additionally, the use of single component fluids or azeotrope-like mixtures, which do not substantially fractionate on boiling and evaporation, is desirable in certain circumstances.

As suggested above, concern has been increasing in recent years about potential damage to the earth's atmosphere and climate, and certain chlorine-based compounds have been identified as particularly problematic in this regard. The use of chlorine-containing compositions (such as chlorofluorocarbons (CFC's), hydrochlorofluorocarbons (HCF's) and the like) as the working fluid in heat transfer systems, such as in refrigeration and air-conditioning systems, has become disfavored because of the ozone-depleting properties associated with many of such compounds. There has thus been an increasing need for new fluorocarbon and hydrofluorocarbon compounds and compositions that are attractive alternatives to the compositions heretofore used in these and other applications. For example, it has become desirable to retrofit chlorine-containing systems, such as blowing agent systems or refrigeration systems, by replacing chlorine-containing compounds with non-chlorine-containing compounds that will not deplete the ozone layer, such as hydrofluorocarbons (HFC's). Industry in general is continually seeking new fluorocarbon based mixtures that offer alternatives to, and are considered environmentally safer substitutes for, CFCs and HCFCs. It is considered important in many cases, however, that any potential substitute must also possess those properties present in many of the most widely used fluids, such as imparting excellent thermal insulating properties and other desirable foam characteristics when used as blowing agents, such as appropriate chemical stability, low- or no-toxicity, low or no-flammability, among others.

Furthermore, it is generally considered desirably for CFC blowing agent substitutes to be effective without major engineering changes to conventional foam generating systems.

Methods and compositions for making conventional foamed materials, such as for example thermoplastic materials and thermosetting materials, have long been known. These methods and compositions have typically utilized chemical and/or physical blowing agents to form the foamed structure in a polymeric matrix. Such blowing agents have included, for example, azo compounds, various volatile organic compounds (VOCs) and chlorofluorocarbons (CFCs). The chemical blowing agents typically undergo some form of chemical change, including chemical reaction with the material that forms the polymer matrix (usually at a predetermined temperature/pressure) that causes the release of a gas, such as nitrogen, carbon dioxide, or carbon monoxide. One of the most frequently used chemical blowing agents is water. The physical blowing agents typically are dissolved in the polymer or polymer precursor material and then expand volumetrically (again at a predetermined temperature/pressure) to contribute to the formation of the foamed structure. Physical blowing agents are frequently used in connection with thermoplastic foams, although chemical blowing agents can be used in place of or in addition to physical blowing agents in connection with thermoplastic foam. For example, it is known to use chemical blowing agent in connection with the formation of polyvinylchloride-based foams. It is common to use chemical blowing and/or physical blowing agents in connection with thermosetting foams. Of course, it is possible that certain compounds and the compositions that contain them may at once constitute a chemical and a physical blowing agent.

It was common in the past that the CFCs were used as standard blowing agents in the preparation of isocyanate-based foams, such as rigid and flexible polyurethane and polyisocyanurate foams. For example, $CCl_3F$ (CFC-11) had become a standard blowing agent. However, the use of this material has been banned by international treaty on the grounds that its release into the atmosphere damages the ozone layer in the stratosphere. As a consequence, it is no longer generally common that neat CFC-11 is used as a standard blowing agent for forming thermosetting foams, such as isocyanate-based foams and phenolic foams.

The problems with CFCs led to the more frequent utilization hydrogen-containing chlorofluoroalkanes (HCFCs). For example, $CHCl_2CF_3$ (HCFC-123), $CH_2ClCHClF$ (HCFC-141b) have relatively short lifetimes in the atmosphere. However, while HCFCs are considered to be environmentally friendly blowing agents relative to CFCs, such compounds still contain some chlorine, and therefore have an "Ozone Depletion Potential" (called "ODP"). Because of the non-zero ODP, HCFCs have been targeted for eventual removal from use.

Another known class of blowing agents is the non-chlorinated, partially hydrogenated fluorocarbons (called "HFCs"). Certain of the HFC currently being used as blowing agents have at least one potentially serious problem, namely that they generally have relatively high intrinsic thermal conductivity properties (i.e., poor thermal insulation). On the other hand, foams made with certain of the more modern HFC blowing agents, such as $CF_3CH_2CF_2H$ ("HFC-245fa") offer improved thermal insulation, due in part to the low thermal conductivity of HFC-245fa vapor, and due in part to the fine cell structure HFC-245fa imparts to the foams. HFC-245fa has been widely used in insulation applications, particularly refrigerator, freezer, refrigerator/freezer and spray foam applications. Nevertheless, many HFC fluids share the disadvantage of having relatively high global warming potentials, and it is desirable to use hydrofluorocarbon or other fluorinated fluids having as low global warming potentials as possible while maintaining the desired performance in use properties. Even the more modern HFCs, such as HFC-245fa, HFC-134a, HFC-365mfc, and others, exhibit a higher than desirable global warming potential, albeit low relative to other HFCs. Thus, the use of HFCs as blowing agents in foam insulation, particularly rigid foam insulation, has resulted in HFCs being less desirable candidates for blowing agents in commercial foam insulation.

Hydrocarbon blowing agents are also known. For example, U.S. Pat. No. 5,182,309 to Hutzen teaches the use of iso- and normal-pentane in various emulsion mixtures. Another example of hydrocarbon blowing agents is cyclopentane, as taught by U.S. Pat. No. 5,096,933—Volkert. Although many hydrocarbon blowing agents, such as cyclopentane, and isomers of pentane, are zero ozone depleting agents and exhibit very low global warming potential, such material are less than fully desirable because foams produced from these blowing agents lack the same degree of thermal insulation efficiency as foams made with, for example, HFC-245fa blowing agent. Further, the hydrocarbon blowing agents are extremely flammable, which is undesirable. Also, certain hydrocarbon blowing agents have inadequate miscibility in certain situations with material from which the foam is formed, such as many of the polyester polyols commonly used in polyisocyanurate modified polyurethane foam. The use of these alkanes frequently requires a chemical surfactant to obtain a suitable mixture.

There has thus been an increasing need for new compounds and compositions that are attractive alternatives to the compositions heretofore used as blowing agents in these and other applications. Applicants have thus recognized a need for new fluorocarbon based compounds and compositions that offer effective alternatives to, and are considered environmentally safer substitutes for, CFCs and HCFCs. It is generally considered highly desirable, however, that any potential substitute must also possess properties, or impart properties to the foam, that are at least comparable to those associated with many of the most widely used blowing agents, such as vapor phase thermal conductivity (low k-factor), low- or no-toxicity, among others.

One such other potentially important property in many applications is flammability. That is, it is considered either important or essential in many applications, including particularly in blowing agent applications, to use compositions which are of low flammability or are non-flammable. As used herein, the term "nonflammable" refers to compounds or compositions which are determined to be nonflammable as determined in accordance with ASTM standard E-681, dated 2002, which is incorporated herein by reference. Unfortunately, many HFC's which might otherwise be desirable for used in refrigerant compositions are not nonflammable. For example, the fluoroalkane difluoroethane (HFC-152a) and the fluoroalkene 1,1,1-trifluorpropene (HFO-1243zf) are each flammable and therefore not viable for use in many applications.

It has been suggested to use bromine-containing halocarbon additives to decrease flammability of certain materials, including foam blowing agents, in U.S. Pat. No. 5,900,185—Tapscott. The additives in this patent are said to be characterized by high efficiency and short atmospheric lifetimes, that is, low ozone depletion potential (ODP) and a low global warming potential (GWP).

While the brominated olefins described in Tapscott may have some level of effectiveness as anti-flammability agents in connection with certain materials, there is no disclosure of the use of such materials as a blowing agent. Furthermore, it is believed that such compounds may also have certain disadvantages. For example, applicants have come to recognize that many of the compounds identified in Tapscott will have a relatively low efficiency as a blowing agent due to the relatively high molecular weight of such compounds. In addition, it is believed that many of the compounds disclosed in Tapscott will encounter problems when used as a blowing agent due to the relatively high boiling point of such compounds. Moreover, it is understood by applicants that many compounds which have a high level of substitution may possess undesirable toxicity properties and/or other undesirable properties, such as potentially environmentally undesirable bioaccumulation.

While Tapscott indicates that bromine-containing alkenes having from 2 to 6 carbon atoms may also contain fluorine substituents, this patent appears to suggest that fluorine-containing compounds are less than fully desirable from the standpoint of environmental safety by noting that "non-fluorine-containing bromoalkanes will have very short atmospheric lifetimes due to reaction with tropospheric hydroxyl free radicals." (Col. 8, l. 34-39).

Furthermore, it is generally considered desirable for blowing agent substitutes to be effective without major engineering changes to conventional equipment and systems used in foam preparation and formation.

Applicants have thus come to appreciate a need for compositions, and particularly blowing agents, foamable compostions, foamed articles and methods and systems for forming foam, which provide beneficial properties and/or avoid one or more of the disadvantages noted above. Applicants have thus come to appreciate a need for compositions, and particularly blowing agents, that are potentially useful in numerous applications, while avoiding one or more of the disadvantages noted above.

This invention relates to compositions, methods and systems having utility in numerous applications, including particularly in connection with compositions, methods, systems and agents relating to polymeric foams.

BRIEF DESCRIPTION OF THE DRAWINGS

FIG. 1 provides a sketch of the vessel as discussed in Example 1A.

SUMMARY

Applicants have found that the above-noted need, and other needs, can be satisfied by blowing agent compositions, foamable compositions, foams and/or foamed articles comprising one or more C2 to C6 fluoroalkenes, more preferably one or more C3 to C5 fluoroalkenes, and even more preferably one or more compounds having Formula I as follows:

$$XCF_zR_{3-z} \tag{1}$$

where X is a $C_1$, $C_2$, $C_3$, $C_4$, or $C_5$ unsaturated, substituted or unsubstituted, radical, each R is independently Cl, F, Br, I or H, and z is 1 to 3, it generally being preferred that the fluoroalkene of the present invention has at least four (4) halogen substituents, at least three of which are F and even more preferably none of which are Br.

For embodiments in which at least one Br substituent is present, it is preferred that the compound includes no hydrogen. In such embodiments it also generally preferred that the Br substituent is on an unsaturated carbon, and even more preferably the Br substituent is on a non-terminal unsaturated carbon. One particularly preferred compound in this class is $CF_3CBr=CF_2$, including all of its isomers In certain embodiments it is highly preferred that the compounds of Formula I are propenes, butenes, pentenes and hexenes having from 3 to 5 fluorine substituents, with other substituents being either present or not present. In certain preferred embodiments, no R is Br, and preferably the unsaturated radical contains no Br substituents. Among the propenes, tetrafluoropropenes (HFO-1234) and fluorochloroporpenes (such as trifluoro, monochloropropenes (HFCO-1233)), and even more preferably $CF_3CCl=CH_2$ (HFO-1233xf) and $CF_3CH=CHCl$ (HFO-1233zd)) are especially preferred in certain embodiments.

In certain embodiments, pentafluoropropenes are preferred, including particularly those pentafluoropropenes in which there is a hydrogen substituent on the terminal unsaturated carbon, such as $CF_3CF=CFH$ (HFO-1225yez), particularly since applicants have discovered that such compounds have a relatively low degree of toxicity in comparison to at least the compound $CF_3CH=CF_2$ (HFO-1225zc).

Among the butenes, fluorochlorobutenes are especially preferred in certain embodiments.

The term "HFO-1234" is used herein to refer to all tetrafluoropropenes. Among the tetrafluoropropenes are included 1,1,1,2-tetrafluoropropene (HFO-1234yf) and both cis- and trans-1, 1, 1, 3-tetrafluoropropene (HFO-1234ze). The term HFO-1234ze is used herein generically to refer to 1,1,1,3-tetrafluoropropene, independent of whether it is the cis- or trans-form. The terms "cisHFO-1234ze" and "transHFO-1234ze" are used herein to describe the cis- and trans-forms of 1,1,1,3-tetrafluoropropene respectively. The term "HFO-1234ze" therefore includes within its scope cisHFO-1234ze, transHFO-1234ze, and all combinations and mixtures of these.

The term "HFO-1233" is used herein to refer to all trifluoro,monochloropropenes. Among the trifluoro,monochloropropenes are included 1,1,1,trifluoro-2,chloro-propene (HFCO-1233xf) and both cis- and trans-1,1,1-trifluo-3, chlororopropene (HFCO-1233zd). The term HFCO-1233zd is used herein generically to refer to 1,1,1-trifluo-3,chloropropene, independent of whether it is the cis- or trans-form. The terms "cisHFCO-1233zd" and "transHFCO-1233zd" are used herein to describe the cis- and trans-forms of 1, 1, 1-trifluo,3-chlororopropene, respectively. The term "HFCO-1233zd" therefore includes within its scope cisHFCO-1233zd, transHFCO-1233zd, and all combinations and mixtures of these.

The term "HFO-1225" is used herein to refer to all pentafluoropropenes. Among such molecules are included 1,1,1,2,3 pentafluoropropene (HFO-1225yez), both cis- and trans-forms thereof. The term HFO-1225yez is thus used herein generically to refer to 1,1,1,2,3 pentafluoropropene, independent of whether it is the cis- or trans-form. The term "HFO-1225yez" therefore includes within its scope cisHFO-1225yez, transHFO-1225yez, and all combinations and mixtures of these.

The present invention provides also methods and systems which utilize the compositions of the present invention, including methods and systems for foam blowing.

DETAILED DESCRIPTION OF PREFERRED EMBODIMENTS

The Compositions

The present compositions can generally be in the form of blowing agent compositions or foamable compositions. In each case, the present invention requires at least one fluoroalkene compound as described herein and optionally other ingredients, some of which are described in detail below.

A. The Fluoroalkenes

The preferred embodiments of the present invention are directed to compositions comprising at least one fluoroalkene containing from 2 to 6, preferably 3 to 5 carbon atoms, more preferably 3 to 4 carbon atoms, and in certain embodiments most preferably three carbon atoms, and at least one carbon-carbon double bond. The fluoroalkene compounds of the present invention are sometimes referred to herein for the purpose of convenience as hydrofluoro-olefins or "HFOs" if they contain at least one hydrogen. Although it is contemplated that the HFOs of the present invention may contain two carbon—carbon double bonds, such compounds at the present time are not considered to be preferred. For HFOs which also contain at least one chlorine atom, the designation HFCO is sometimes used herein As mentioned above, the present compositions comprise one or more compounds in accordance with Formula I. In preferred embodiments, the compositions include one or more compounds of Formula II below:

(II)

where each R is independently Cl, F, Br, I or H
R' is $(CR_2)_nY$,
Y is $CRF_2$
and n is 0, 1, 2 or 3, preferably 0 or 1, it being generally preferred however that either Br is not present in the compound or when Br is present in the compound there is no hydrogen in the compound.

In highly preferred embodiments, Y is $CF_3$, n is 0 or 1 (most preferably 0) and at least one of the remaining Rs is F, and preferably no R is Br, or when Br is present there is no hydrogen in the compound. It is preferred in certain cases that no R in Formula II is Br.

Applicants believe that, in general, the compounds of the above identified Formulas I and II are generally effective and exhibit utility in blowing agent compositions in accordance with the teachings contained herein. However, applicants have surprisingly and unexpectedly found that certain of the compounds having a structure in accordance with the formulas described above exhibit a highly desirable low level of toxicity compared to other of such compounds. As can be readily appreciated, this discovery is of potentially enormous advantage and benefit for the formulation of blowing agent compositions. More particularly, applicants believe that a relatively low toxicity level is associated with compounds of Formula I or Formula II (preferably wherein Y is $CF_3$, n is 0 or 1) wherein at least one R on the unsaturated terminal carbon is H, and at least one of the remaining Rs is F or Cl. Applicants believe also that all structural, geometric and stereoisomers of such compounds are effective and of beneficially low toxicity.

In certain preferred embodiments, the compound of the present invention comprises a $C_3$ or $C_4$ HFO or HFCO, preferably a $C_3$ HFO, and more preferably a compound in accordance with Formula I in which X is a halogen substituted $C_3$ alkylene and z is 3. In certain of such embodiments X is fluorine and/or chlorine substituted $C_3$ alkylene, with the following $C_3$ alkylene radicals being preferred in certain embodiments:

—CH=CF—$CH_3$
—CF=CH—$CH_3$
—$CH_2$—CF=$CH_2$
—$CH_2$—CH=CFH,

Such embodiments therefore comprise the following preferred compounds: $CF_3$—CH=CF—$CH_3$; $CF_3$—CF=CH—$CH_3$; $CF_3$—$CH_2$—CF=$CH_2$; $CF_3$—$CH_2$—CH=CFH; and combinations of these with one another and/or with other compounds in accordance with Formula I or Formula II.

In certain preferred embodiments, the compound of the present invention comprises a $C_3$ or $C_4$ HFCO, preferably a $C_3$ HFCO, and more preferably a compound in accordance with Formula II in which Y is $CF_3$, n is 0, at least one R on the unsaturated terminal carbon is H, and at least one of the remaining Rs is Cl. HFCO-1233 is an example of such a preferred compound.

In highly preferred embodiments, especially embodiments which comprise the low toxicity compounds described above, n is zero. In certain highly preferred embodiments the compositions of the present invention comprise one or more tetrafluoropropenes, including HFO-1234yf, (cis)HFO-1234ze and (trans)HFO-1234ze, with HFO-1234ze being generally preferred and trans HFO-1234ze being highly preferred in certain embodiments. Although the properties of (cis)HFO-1234ze and (trans)HFO-1234ze differ in at least some respects, it is contemplated that each of these compounds is adaptable for use, either alone or together with other compounds including its stereo isomer, in connection with each of the applications, methods and systems described herein. For example, (trans)HFO-1234ze may be preferred for use in certain systems because of its relatively low boiling point (−19° C.), while (cis)HFO-1234ze, with a boiling point of +9° C., may be preferred in other applications. Of course, it is likely that combinations of the cis- and trans-isomers will be acceptable and/or preferred in many embodiments. Accordingly, it is to be understood that the terms "HFO-1234ze" and 1,3,3,3-tetrafluoropropene refer to both stereo isomers, and the use of this term is intended to indicate that each of the cis- and trans-forms applies and/or is useful for the stated purpose unless otherwise indicated.

HFO-1234 compounds are known materials and are listed in Chemical Abstracts databases. The production of fluoropropenes such as $CF_3CH=CH_2$ by catalytic vapor phase fluorination of various saturated and unsaturated halogen-containing $C_3$ compounds is described in U.S. Pat. Nos. 2,889,379; 4,798,818 and 4,465,786, each of which is incorporated herein by reference. EP 974,571, also incorporated herein by reference, discloses the preparation of 1,1,1,3-tetrafluoropropene by contacting 1,1,1,3,3-pentafluoropropane (HFC-245fa) in the vapor phase with a chromium-based catalyst at elevated temperature, or in the liquid phase with an alcoholic solution of KOH, NaOH, $Ca(OH)_2$ or $Mg(OH)_2$. In addition, methods for producing compounds in accordance with the present invention are described generally in connection with pending U.S. patent application Ser. No. 15/893,955, entitled "Process for Producing Fluorpropenes", which is also incorporated herein by reference.

Other preferred compounds for use in accordance with the present invention include pentafluoropropenes, including all isomers thereof (eg., HFO-1225), tetra- and penta-fluorobutenes, including all isomers thereof (eg., HFO-1354 and HFO-1345). Of course, the present compositions may comprise combinations of any two or more compounds within the broad scope of the invention or within any preferred scope of the invention.

The present compositions, particularly those comprising HFO-1234 (including HFO-1234ze and HFO-1234yf), are believed to possess properties that are advantageous for a number of important reasons. For example, applicants believe, based at least in part on mathematical modeling, that the fluoroolefins of the present invention will not have a substantial negative affect on atmospheric chemistry, being negligible contributors to ozone depletion in comparison to some other halogenated species. The preferred compositions of the present invention thus have the advantage of not contributing substantially to ozone depletion. The preferred compositions also do not contribute substantially to global warming compared to many of the hydrofluoroalkanes presently in use.

In certain preferred forms, compositions of the present invention have a Global Warming Potential (GWP) of not greater than about 1000, more preferably not greater than about 500, and even more preferably not greater than about 150. In certain embodiments, the GWP of the present compositions is not greater than about 100 and even more preferably not greater than about 75. As used herein, "GWP" is measured relative to that of carbon dioxide and over a 100 year time horizon, as defined in "The Scientific Assessment of Ozone Depletion, 2002, a report of the World Meteorological Association's Global Ozone Research and Monitoring Project," which is incorporated herein by reference.

In certain preferred forms, the present compositions also preferably have an Ozone Depletion Potential (ODP) of not greater than 0.05, more preferably not greater than 0.02 and even more preferably about zero. As used herein, "ODP" is as defined in "The Scientific Assessment of Ozone Depletion, 2002, A report of the World Meteorological Association's Global Ozone Research and Monitoring Project," which is incorporated herein by reference.

The amount of the Formula I compounds, particularly HFO-1234 and even more preferably HFO-1234ze, contained in the present compositions can vary widely, depending the particular application, and compositions containing more than trace amounts and less than 100% of the compound are within broad the scope of the present invention. Moreover, the compositions of the present invention can be azeotropic, azeotrope-like or non-azeotropic. In preferred embodiments, the present compositions, particularly blowing agent compositions, comprise Formula I and/or Formula II compounds, preferably HFO-1234 and more preferably HFO-1234ze and/or HFO-1234yf, in amounts from about 1% by weight to about 99% by weight, more preferably from about 5% to about 95% by weight, and even more preferably from 40% to about 90% by weight.

B. Other Components—Blowing Agent Compositions

It is contemplated that in certain embodiments of the present invention the blowing agent compositions consist of or consist essentially of one or more compounds in accordance with Formula I hereof. Thus, the present invention includes methods and systems which include using one or more of the compounds of the present invention as a blowing agent without the presence of any substantial amount of additional components. However, one or more compounds or components that are not within the scope of Formula I or Formula II are optionally, but preferably, included in the blowing agent compositions of the present invention. Such optional additional compounds include, but are not limited to, other compounds which also act as blowing agents (hereinafter referred to for convenience but not by way of limitation as co-blowing agents), surfactants, polymer modifiers, toughening agents, colorants, dyes, solubility enhancers, rheology modifiers, plasticizing agents, flammability suppressants, antibacterial agents, viscosity reduction modifiers, fillers, vapor pressure modifiers, nucleating agents, catalysts and the like. In certain preferred embodiments, dispersing agents, cell stabilizers, surfactants and other additives may also be incorporated into the blowing agent compositions of the present invention. Certain surfactants are optionally but preferably added to serve as cell stabilizers. Some representative materials are sold under the names of DC-193, B-8404, and L-5340 which are, generally, polysiloxane polyoxyalkylene block co-polymers such as those disclosed in U.S. Pat. Nos. 2,834,748, 2,917,480, and 2,846,458, each of which is incorporated herein by reference. Other optional additives for the blowing agent mixture may include flame retardants such as tri(2-chloroethyl)phosphate, tri(2-chloropropyl)phosphate, tri(2,3-dibromopropyl)-phosphate, tri(1,3-dichloropropyl) phosphate, diammonium phosphate, various halogenated aromatic compounds, antimony oxide, aluminum trihydrate, polyvinyl chloride, and the like.

With respect to nucleating agents, all known compounds and materials having nucleating functionality are available for use in the present invention, including particularly talc.

Of course other compounds and/or components that modulate a particular property of the compositions (such as cost for example) may also be included in the present compositions, and the presence of all such compounds and components is within the broad scope of the invention.

Thus, the preferred embodiments of the present compositions include, in addition to the compounds of Formula I (including particularly HFO-1234ze and/or HFO-1234yf), one or more co-blowing agents. The co-blowing agent in accordance with the present invention can comprise a physical blowing agent, a chemical blowing agent (which preferably in certain embodiments comprises water) or a blowing agent having a combination of physical and chemical blowing agent properties. It will also be appreciated that the blowing agents included in the present compositions, including the compounds of Formula I as well as the co-blowing agent, may exhibit properties in addition to those required to be characterized as a blowing agent. For example, it is contemplated that the blowing agent compositions of the present invention may include components, including the compounds or Formula I described above, which also impart some beneficial property to the blowing agent composition or to the foamable composition to which it is added. For example, it is within the scope of the present invention for the compound of Formula I or for the co-blowing agent to also act as a polymer modifier or as a viscosity reduction modifier.

Although it is contemplated that a wide range of co-blowing agents may be used in accordance with the present invention, in certain embodiments it is preferred that the blowing agent compositions of the present invention include one or more HFCs as co-blowing agents, more preferably one or more C1-C4 HFCs, and/or one or more hydrocarbons, more preferably C4-C6 hydrocarbons. For example, with respect to HFCs, the present blowing agent compositions may include one or more of difluoromethane (HFC-32), fluoroethane (HFC-161), difluoroethane (HFC-152), trifluoroethane (HFC-143), tetrafluoroethane (HFC-134), pentafluoroethane (HFC-125), pentafluoropropane (HFC-245), hexafluoropropane (HFC-236), heptafluoropropane (HFC-227ea), pentafluorobutane (HFC-365), hexafluorobutane (HFC-356) and all isomers of all such HFC's. With respect to hydrocarbons, the present blowing agent compositions may include in certain preferred embodiments, for example, iso, normal and/or cyclopentane for thermoset foams and butane or isobutane for thermoplastic foams. Of course other materials, such as water, $CO_2$, CFCs (such as trichlorofluoromethane (CFC-11) and dichlorodifluoromethane (CFC-12)), hydrochlorocarbons (HCCs such as dichloroethylene (preferably trans-dichloroethylene), ethyl chloride and chloropropane), HCFCs, C1-C5 alcohols (such as, for example, ethanol and/or propanol and/or butanol), C1-C4 aldehydes, C1-C4 ketones, C1-C4 ethers (including ethers (such as dimethyl ether and diethyl ether), diethers (such as dimethoxy methane and diethoxy methane)), and methyl formate including combinations of any of these may be included, although such components are contemplated to be not preferred in many embodiments due to negative environmental impact.

In certain embodiments, one or more of the following HFC isomers are preferred for use as co-blowing agents in the compositions of the present invention:

1,1,1,2,2-pentafluoroethane (HFC-125)
1,1,2,2-tetrafluoroethane (HFC-134)
1,1,1,2-tetrafluoroethane (HFC-134a)
1,1-difluoroethane (HFC-152a)
1,1,1,2,3,3,3-heptafluoropropane (HFC-227ea)
1,1,1,3,3,3-hexafluoropropane (HFC-236fa)
1,1,1,3,3-pentafluoropropane (HFC-245fa) and
1,1,1,3,3-pentafluorobutane (HFC-365mfc).

The relative amount of any of the above noted additional co-blowing agents, as well as any additional components which may be included in present compositions, can vary widely within the general broad scope of the present invention according to the particular application for the composition, and all such relative amounts are considered to be within the scope hereof. Applicants note, however, that one particular advantage of at least certain of the compounds of Formula I in accordance with the present invention, for example HFO-1234ze, is the relatively low flammability of such compounds. Accordingly, in certain embodiments it is preferred that the blowing agent composition of the present invention comprise at least one co-blowing agent and an amount of compound(s) in accordance with Formula I sufficient to produce a blowing agent composition which is overall nonflammable. Thus, in such embodiments, the relative amounts of the co-blowing agent in comparison to the compound of Formula I will depend, at least in part, upon the flammability of the co-blowing agent.

The blowing agent compositions of the present invention may include the compounds of the present invention in widely ranging amounts. It is generally preferred, however, that for preferred compositions for use as blowing agents in accordance with the present invention, compound(s) in accordance with Formula I, and even more preferably Formula II, are present in an amount that is at least about 1% by weight, more preferably at least about 5% by weight, and even more preferably at least about 15% by weight, of the composition. In certain preferred embodiments, the blowing agent comprises at least about 50% by weight of the present blowing agent compound(s), and in certain embodiments the blowing agent consists essentially of compounds in accordance with the present invention. In this regard it is noted that the use of one or more co-blowing agents is consistent with the novel and basic features of the present invention. For example, it is contemplated that water will be used as either a co-blowing or in combination with other co-blowing agents (such as, for example, pentane, particularly cyclopentane) in a large number of embodiments.

It is contemplated that the blowing agent compositions of the present invention may comprise, preferably in amounts of at least about 15% by weight of the composition, HFO-1234yf, cisHFO-1234ze, transHFO1234ze or combinations of two or more of these. In many preferred embodiments, a co-blowing agent comprising water is included in the compositions, most preferably in compositions directed to the use of thermosetting foams. In certain preferred embodiments, the blowing agent compositions of the present invention comprise a combination of cisHFO-1234ze and transHFO1234ze in a cis:trans weight ratio of from about 1:99 to about 50:50, more preferably from about 10:90 to about 30:70. In certain embodiments, it may be preferred to use a combination of cisHFO-1234ze and transHFO1234ze in a cis:trans weight ratio of from about 1:99 to about 10:90, and preferably from about 1:99 to about 5:95. Of course, it may be desirable in certain embodiments to use combinations in which the cis-isomer is present in a higher concentration than the trans-isomer, as may be the case, for example, for use with foamable compositions adapted for use with liquid blowing agents.

In certain preferred embodiments, the blowing agent composition comprises from about 30% to about 95% by weight of a compound of Formula I, more preferably a compound of Formula II, and even more preferably one or more HFO-1234 compounds, and from about 5% to about 90% by weight, more preferably from about 5% to about 65% by weight of co-blowing agent. In certain of such embodiments the co-blowing agent comprises, and preferably consists essentially of, $H_2O$, HFCs, hydrocarbons, alcohols (preferably C2, C3 and/or C4 alcohols), $CO_2$, and combinations of these.

In preferred embodiments in which the co-blowing agent comprises $H_2O$, the composition comprises $H_2O$ in an amount of from about 5% by weight to about 50% by weight of the total blowing agent composition, more preferably from about 10% by weight to about 40% by weight, and even more preferably of from about 10% to about 20% by weight of the total blowing agent.

In preferred embodiments in which the co-blowing agent comprises $CO_2$, the composition comprises $CO_2$ in an amount of from about 5% by weight to about 60% by weight of the total blowing agent composition, more preferably from about 20% by weight to about 50% by weight, and even more preferably of from about 40% to about 50% by weight of the total blowing agent.

In preferred embodiments in which the co-blowing agent comprises alcohols, (preferably C2, C3 and/or C4 alcohols), the composition comprises alcohol in an amount of from about 5% by weight to about 40% by weight of the total blowing agent composition, more preferably from about 10% by weight to about 40% by weight, and even more preferably of from about 15% to about 25% by weight of the total blowing agent.

For compositions which include HFC co-blowing agents, the HFC co-blowing agent (preferably C2, C3, C4 and/or C5 HFC), and even more preferably difluoromethane (HFC-152a) (HFC-152a being particularly preferred for extruded thermoplastics) and/or pentafluoropropane (HFC-245)), is preferably present in the composition in amounts of from of from about 5% by weight to about 80% by weight of the total blowing agent composition, more preferably from about 10% by weight to about 75% by weight, and even more preferably of from about 25% to about 75% by weight of the total blowing agent. Furthermore, in such embodiments, the HFC is preferably C2-C4 HFC, and even more preferably C3 HFC, with penta-fluorinated C3 HFC, such as HFC-245fa, being highly preferred in certain embodiments.

For compositions which include HC co-blowing agents, the HC co-blowing agent (preferably C3, C4 and/or C5 HC) is preferably present in the composition in amounts of from of from about 5% by weight to about 80% by weight of the total blowing agent composition, and even more preferably from about 20% by weight to about 60% by weight of the total blowing agent.

C. Other Components—Foamable Compositions

One aspect of the present invention provides foamable compositions. As is known to those skilled in the art, foamable compositions generally include one or more components capable of forming foam. As used herein, the term "foam foaming agent" is used to refer to a component, or a combination on components, which are capable of forming a foam structure, preferably a generally cellular foam structure. The foamable compositions of the present invention include such component(s) and a blowing agent compound, preferably a compound of Formula I, in accordance with the present invention. In certain embodiments, the one or more components capable of forming foam comprise a thermosetting composition capable of forming foam and/or foamable compositions. Examples of thermosetting compositions include polyurethane and polyisocyanurate foam compositions, and also phenolic foam compositions. This reaction and foaming process may be enhanced through the use of various additives such as catalysts and surfactant materials that serve to control and adjust cell size and to stabilize the foam structure during formation. Furthermore, is contemplated that any one or more of the additional components described above with respect to the blowing agent compositions of the present invention could be incorporated into the foamable composition of the present invention. In such thermosetting foam embodiments, one or more of the present compositions are included as or part of a blowing agent in a foamable composition, or as a part of a two or more part foamable composition, which preferably includes one or more of the components capable of reacting and/or foaming under the proper conditions to form a foam or cellular structure.

In certain other embodiments of the present invention, the one or more components capable of foaming comprise thermoplastic materials, particularly thermoplastic polymers and/or resins. Examples of thermoplastic foam components include polyolefins, such as for example monovinyl aromatic compounds of the formula Ar—CHCH2 wherein Ar is an aromatic hydrocarbon radical of the benzene series such as polystyrene (PS). Other examples of suitable polyolefin resins in accordance with the invention include the various ethylene resins including the ethylene homopolymers such as polyethylene and ethylene copolymers, polypropylene (PP) and polyethyleneterepthalate (PET). In certain embodiments, the thermoplastic foamable composition is an extrudable composition.

Methods and Systems

It is contemplated that all presently known and available methods and systems for forming foam are readily adaptable for use in connection with the present invention. For example, the methods of the present invention generally require incorporating a blowing agent in accordance with the present invention into a foamable or foam forming composition and then foaming the composition, preferably by a step or series of steps which include causing volumetric expansion of the blowing agent in accordance with the present invention. In general, it is contemplated that the presently used systems and devices for incorporation of blowing agent and for foaming are readily adaptable for use in accordance with the present invention. In fact, it is believed that one advantage of the present invention is the provision of an improved blowing agent which is generally compatible with existing foaming methods and systems.

Thus, it will be appreciated by those skilled in the art that the present invention comprises methods and systems for foaming all types of foams, including thermosetting foams, thermoplastic foams and formed-in-place foams. Thus, one aspect of the present invention is the use of the present blowing agents in connection conventional foaming equipment, such as polyurethane foaming equipment, at conventional processing conditions. The present methods therefore include masterbatch type operations, blending type operations, third stream blowing agent addition, and blowing agent addition at the foam head.

With respect to thermoplastic foams, the preferred methods generally comprise introducing a blowing agent in accordance with the present invention into a thermoplastic material, preferably thermoplastic polymer such as polyolefin, and then subjecting the thermoplastic material to conditions effective to cause foaming. For example, the step of introducing the blowing agent into the thermoplastic material may comprise introducing the blowing agent into a screw extruder containing the thermoplastic, and the step of causing foaming may comprise lowering the pressure on the thermoplastic material and thereby causing expansion of the blowing agent and contributing to the foaming of the material.

It will be appreciated by those skilled in the art, especially in view of the disclosure contained herein, that the order and manner in which the blowing agent of the present invention is formed and/or added to the foamable composition does not generally affect the operability of the present invention. For example, in the case of extrudable foams, it is possible that the various components of the blowing agent, and even the components of the foamable composition, be not be mixed in advance of introduction to the extrusion equipment, or even that the components are not added to the same location in the extrusion equipment. Moreover, the blowing agent can be introduced either directly or as part of a premix, which is then further added to other parts of the foamable composition.

Thus, in certain embodiments it may be desired to introduce one or more components of the blowing agent at first location in the extruder, which is upstream of the place of addition of one or more other components of the blowing agent, with the expectation that the components will come together in the extruder and/or operate more effectively in this manner. Nevertheless, in certain embodiments, two or more components of the blowing agent are combined in advance and introduced together into the foamable composition, either directly or as part of premix which is then further added to other parts of the foamable composition.

One embodiment of the present invention relates to methods of forming foams, and preferably polyurethane and polyisocyanurate foams. The methods generally comprise providing a blowing agent composition of the present inventions, adding (directly or indirectly) the blowing agent composition to a foamable composition, and reacting the foamable composition under the conditions effective to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, NY, which is incorporated herein by reference, may be used or adapted for use in accordance with the foam embodiments of the present invention. In general, such preferred methods comprise preparing polyurethane or polyisocyanurate foams by combining an isocyanate, a polyol or mixture of polyols, a blowing agent or mixture of blowing agents comprising one or more of the present compositions, and other materials such as catalysts, surfactants, and optionally, flame retardants, colorants, or other additives.

It is convenient in many applications to provide the components for polyurethane or polyisocyanurate foams in pre-blended formulations. Most typically, the foam formulation is pre-blended into two components. The isocyanate and optionally certain surfactants and blowing agents comprise the first component, commonly referred to as the "A" component. The polyol or polyol mixture, surfactant, catalysts, blowing agents, flame retardant, and other isocyanate reactive components comprise the second component, commonly referred to as the "B" component. Accordingly, polyurethane or polyisocyanurate foams are readily prepared by bringing together the A and B side components either by hand mix for small preparations and, preferably, machine mix techniques to form blocks, slabs, laminates, pour-in-place panels and other items, spray applied foams, froths, and the like. Optionally, other ingredients such as fire retardants, colorants, auxiliary blowing agents, and even other polyols can be added as one or more additional streams to the mix head or reaction site. Most preferably, however, they are all incorporated into one B-component as described above.

The present methods and systems also include forming a one component foam, preferably polyurethane foam, containing a blowing agent in accordance with the present invention. In certain preferably embodiments, a portion of the blowing agent is contained in the foam forming agent, preferably by being dissolved in a foam forming agent which is liquid at the pressure within the container, a second portion of the blowing agent is present as a separate gas phase. In such systems, the contained/dissolved blowing agent performs, in large part, to cause the expansion of the foam, and the separate gas phase operates to impart propulsive force to the foam forming agent. Such one component systems are typically and preferably packaged in a container, such as an aerosol type can, and the blowing agent of the present invention thus preferably provides for expansion of the foam and/or the energy to transport the foam/foamable material from the package, and preferably both. In certain embodiments, such systems and methods comprise charging the package with a fully formulated system (preferably isocyanate/polyol system) and incorporating a gaseous blowing agent in accordance with the present invention into the package, preferably an aerosol type can.

Any of the methods well known in the art, such as those described in "Polyurethanes Chemistry and Technology," Volumes I and II, Saunders and Frisch, 1962, John Wiley and Sons, New York, NY, which is incorporated herein by reference, may be used or adapted for use in accordance with the foam forming embodiments of the present invention.

It is contemplated also that in certain embodiments it may be desirable to utilize the present compositions when in the supercritical or near supercritical state as a blowing agent.

The Foams

The invention also relates to all foams, (including but not limited to closed cell foam, open cell foam, rigid foam, flexible foam, integral skin and the like) prepared from a polymer foam formulation containing a blowing agent comprising the compositions of the invention. Applicants have found that one advantage of the foams, and particularly thermoset foams such as polyurethane foams, in accordance with the present invention is the ability to achieve, preferably in connection with thermoset foam embodiments, exceptional thermal performance, such as can be measured by the K-factor or lambda, particularly and preferably under low temperature conditions. Although it is contemplated that the present foams, particularly thermoset foams of the present invention, may be used in a wide variety of applications, in certain preferred embodiments the present invention comprises appliance foams in accordance with the present invention, including refrigerator foams, freezer foams, refrigerator/freezer foams, panel foams, and other cold or cryogenic manufacturing applications.

The foams in accordance with the present invention, in certain preferred embodiments, provide one or more exceptional features, characteristics and/or properties, including: thermal insulation efficiency (particularly for thermoset foams), dimensional stability, compressive strength, aging of thermal insulation properties, all in addition to the low ozone depletion potential and low global warming potential associated with many of the preferred blowing agents of the present invention. In certain highly preferred embodiments, the present invention provides thermoset foam, including such foam formed into foam articles, which exhibit improved thermal conductivity relative to foams made using the same blowing agent (or a commonly used blowing agent HFC-245fa) in the same amount but without the compound of Formula I in accordance with the present invention. In certain highly preferred embodiments, the thermoset foams, and preferably polyurethane foams, of the present invention exhibit a K-factor (BTU in/hr ft$^{2\circ}$ F.) at 40° F. of not greater than about 0.14, more preferably not greater than 0.135, and even more preferably not greater than 0.13. Furthermore, in certain embodiments, it is preferred that the thermoset foams, and preferably the polyurethane foams of the present invention exhibit a K-factor (BTU in/hr ft$^{2\circ}$ F.) at 75° F. of not greater than about 0.16, more preferably not greater than 0.15, and even more preferably not greater than 0.145.

In other preferred embodiments, the present foams exhibit improved mechanical properties relative to foams produced with blowing agents outside the scope of the present invention. For example, certain preferred embodiments of the present invention provide foams and foam articles having a compressive strength which is superior to, and preferably at least about 10 relative percent, and even more preferably at least about 15 relative percent greater than a foam produced under substantially identical conditions by utilizing a blowing agent consisting of cyclopentane. Furthermore, it is preferred in certain embodiments that the foams produced in accordance with the present invention have compressive strengths that are on a commercial basis comparable to the compressive strength produced by making a foam under substantially the same conditions except wherein the blowing agent consists of HFC-245fa. In certain preferred embodiments, the foams of the present invention exhibit a compressive strength of at least about 12.5% yield (in the parallel and perpendicular directions), and even more preferably at least about 13% yield in each of said directions.

EXAMPLES

The following examples are provided for the purpose of illustrating the present invention but without limiting the scope thereof.

Example 1A—Polystyrene Foam

This example illustrates the use of blowing agent in accordance with two preferred embodiments of the present invention, namely the use of HFO-1234ze and HFO-1234yf, and the production of polystyrene foam. A testing apparatus and protocol has been established as an aid to determining whether a specific blowing agent and polymer are capable of producing a foam and the quality of the foam. Ground polymer (Dow Polystyrene 685D) and blowing agent consisting essentially of HFO-1234ze are combined in a vessel. A sketch of the vessel is illustrated in FIG. 1. The vessel volume is 200 cm$^3$ and it is made from two pipe flanges and a section of 2-inch diameter schedule 40 stainless steel pipe 4 inches long. The vessel is placed in an oven, with temperature set at from about 190° F. to about 285° F., preferably for polystyrene at 265 9F, and remains there until temperature equilibrium is reached.

The pressure in the vessel is then released, quickly producing a foamed polymer. The blowing agent plasticizes the polymer as it dissolves into it. The resulting density of the two foams thus produced using this method are given in Table 1 as the density of the foams produced using trans-HFO-1234ze and HFO-1234yf. The data show that foam polystyrene is obtainable in accordance with the present invention. In this regard it is noted that the bulk density of polystyrene is 1050 kg/m$^3$ or 65.625 lb/ft$^3$ at about room temperature.

TABLE 1

| Foam Formation | Dow polystyrene 685D Foam density (lb/ft$^3$) (at room temperature) | |
| --- | --- | --- |
| Temperature, ° F. | transHFO-1234ze | HFO-1234yf |
| 275 | 55.15 | |
| 260 | 22.14 | 14.27 |
| 250 | 7.28 | 24.17 |
| 240 | 16.93 | |

Example 1B—Polystyrene Foam

This example demonstrates the performance of HFO-1234ze alone as a blowing agent for polystyrene foam formed in a twin screw type extruder. The apparatus employed in this example is a Leistritz twin screw extruder having the following characteristics:

30 mm co-rotating screws

L:D Ratio=40:1

The extruder is divided into 10 sections, each representing a L:D of 4:1. The polystyrene resin was introduced into the first section, the blowing agent was introduced into the sixth section, with the extrudate exiting the tenth section. The extruder operated primarily as a melt/mixing extruder. A subsequent cooling extruder is connected in tandem, for which the design characteristics were:

Leistritz twin screw extruder
40 mm co-rotating screws
L:D Ratio=40:1
Die: 5.0 mm circular Polystyrene resin, namely Nova Chemical—general extrusion grade polystyrene, identified as Nova 1600, is feed to the extruder under the conditions indicated above. The resin has a recommended melt temperature of 375° F.-525° F. The pressure of the extruder at the die is about 1320 pounds per square inch (psi), and the temperature at the die is about 115° C.

A blowing agent consisting essentially of transHFO-1234ze is added to the extruder at the location indicated above, with about 0.5% by weight of talc being included, on the basis of the total blowing agent, as a nucleating agent. Foam is produced using the blowing agent at concentrations of 10% by weight, 12% by weight, and 14% by weight, in accordance with the present invention. The density of the foam produced is in the range of about 0.1 grams per cubic centimeter to 0.07 grams per cubic centimeter, with a cell size of about 49 to about 68 microns. The foams, of approximately 30 millimeters diameter, are visually of very good quality, very fine cell size, with no visible or apparent blow holes or voids.

Example 1C—Polystyrene Foam

This procedure of Example 1B is repeated except that the foaming agent comprises about 50% by weight transHFO-1234ze and 50% by weight of HFC-245fa and nucleating agent in the concentration indicated in Example 1B. Foamed polystyrene is prepared at blowing agent concentrations of approximately 10% and 12%. The density of the foam produced is about 0.09 grams per cubic centimeter, with a cell size of about 200 microns. The foams, of approximately 30 millimeters diameter, are visually of very good quality, fine cell structure, with no visible or apparent voids.

Example 1D—Polystyrene Foam

This procedure of Example 1B is repeated except that the foaming agent comprises about 80% by weight HFO-1234ze and 20% by weight of HFC-245fa and nucleating agent in the concentration indicated in Example 1B. Foamed polystyrene is prepared at blowing agent concentrations of approximately 10% and 12%. The density of the foam produced is about 0.08 grams per cubic centimeter, with a cell size of about 120 microns. The foams, of approximately 30 millimeters diameter, are visually of very good quality, fine cell structure, with no visible or apparent voids.

Example 1E—Polystyrene Foam

This procedure of Example 1B is repeated except that the foaming agent comprises about 80% by weight HFO-124ze and 20% by weight of HFC-245fa and nucleating agent in the concentration indicated in Example 1B. Foamed polystyrene is prepared at blowing agent concentrations of approximately 10% and 12%. The foams' density was in the range of 0.1 grams per cubic centimeter, and. The foams, of approximately 30 millimeters diameter, are visually of very good quality, fine cell structure, with no visible or apparent voids.

Example 1F—Polystyrene Foam

This procedure of Example 1E is repeated except that the nucleating agent is omitted. The foams' density was in the range of 0.1 grams per cubic centimeter, and the cell size diameter is about 400. The foams, of approximately 30 millimeters diameter, are visually of very good quality, fine cell structure, with no visible or apparent voids.

Example 2—Polyurethane Foam Compressive Strength

This example demonstrates the performance of HFO-1234ze, and isomers thereof, used in combination with hydrocarbon co-blowing agents, and in particular the utility of compositions comprising HFO-1234ze and cyclopentane co-blowing agents in compressive strength performance of polyurethane foams.

A commercially available, refrigeration appliance-type polyurethane foam formulation (foam forming agent) is provided. The polyol blend consisted of commercial polyol(s), catalyst(s), and surfactant(s). This formulation is adapted for use in connection with a gaseous blowing agent. Standard commercial polyurethane processing equipment is used for the foam forming process. A gaseous blowing agent combination was formed comprising HFO-1234ze (including isomers thereof) in a concentration of approximately 60 mole percent, and cyclopentane in a concentration of approximately 40 mole percent of the total blowing agent. This example illustrates the physical property performance of combinations of HFO-1234ze (including isomers thereof) in combination with cyclopentane co-blowing agent. Table 2 below reports the compressive strength of similar machine-made polyurethane foams using a blowing agent of the present invention in comparison to foams made using a blowing agent consisting of HFC-245fa and a blowing agent consisting of cyclopentane.

TABLE 2

| Blowing Agent | Compressive Strength | |
|---|---|---|
| | Parallel % Yield | Perpendicular % Yield |
| HFO1234ze/ cyclopentane | 13.513 | 14.672 |
| HFC-245fa | 13.881 | 14.994 |
| Cyclopentane | 11.462 | 10.559 |

One unexpected result illustrated by this example is the ability to process HFO-1234ze, and HFC-1234ze/HFC blends in conventional foam processing equipment, and polyurethane processing equipment in particular. This is potentially of a great advantage in so far that it permits foam processing with various types of systems and equipment, including: masterbatch type blending equipment, gaseous blowing agent blending equipment, third stream addition of the blowing agent, or blowing agent addition at the foam head.

Example 3—Polyurethane Foam K-Factors

A polyurethane foam is prepared and is adapted for use as a commercial "appliance type" polyurethane formulation.

The same foam formulation described in Example 2 is used in connection with the same standard commercial polyurethane processing equipment is used in the foam forming process. Several systems are prepared, with each system using identical components, systems, and equipment, with the exception of the blowing agent. In addition to blowing agent in accordance with the present invention, HFC-134a, HFC-245fa, and cyclopentane are each also tested as the blowing agent. In each system, the blowing agent is added in substantially the same molar concentration into the polyol blend. The polyol blend consists of commercial polyol(s), catalyst(s), and surfactant(s). The foams are prepared in accordance with standard commercial manufacturing operations, for example a commercial operation for making foam for refrigeration applications. The prepared foams were evaluated for k-factor, and this information is reported below in Table 3. For benchmark, comparative purposes, foams were prepared with HFC-134a, for which commercial data can be referenced. The k-factor data for these foams are shown in Table 3.

TABLE 3

| Mean Temperature | k-factor (BTU in/hr ft2 ° F.) | | |
|---|---|---|---|
| (° F.) | HFO-1234ze | HFC-134a | cyclopentane |
| 40 | 0.127 | 0.146 | 0.143 |
| 75 | 0.142 | 0.163 | 0.153 |

This example demonstrates the k-factor performance of HFO-1234ze, and isomers thereof, when HFO-1234ze blowing agent is substituted into the polyurethane formulation. HFO-1234ze was substituted in an equal molar concentration to that of the benchmark foams. Table 3 data illustrates that HFO-1234ze foams k-factors are considerably better than HFC-134a or cyclopentane foams.

Example 4—Polyurethane Foam K-Factors

This example demonstrates the performance of blowing agents comprising HFO-1234ze (including isomers thereof) in combination with various HFC co-blowing agents used in connection with the preparation of polyurethane foams. The same foam formulation, equipment and procedures used in Examples 2 and 3 are used, with the exception of the blowing agent. A blowing agent is prepared comprising HFO-1234ze (including isomers thereof) in a concentration of approximately 80 weight percent of the total blowing agent, and HFC-245fa in a concentration of approximately 20 weight percent of the total blowing agent. In addition to blowing agent in accordance with the present invention, HFC-134a and cyclopentane were each also tested as the blowing agent. In each system, the blowing agent was added in substantially the same molar concentration into the polyol blend. Foams are then formed using this blowing agent and the k-factors of the foam are measured. Table 4 below illustrates the k-factor performance of combinations of HFO-1234ze (including isomers thereof) when used in combination with HFC co-blowing agents.

TABLE 4

| Temperature | k-factor (BTU in/hr ft2 ° F.) | | |
|---|---|---|---|
| (° F.) | HFC-1234ze/ HFC-245fa | HFC-134a | cyclopentane |
| 40 | 0.129 | 0.146 | 0.143 |
| 75 | 0.144 | 0.163 | 0.153 |

One unexpected result illustrated by this example is the ability to process HFO-1234ze, and HFC-1234ze/HFC blends in conventional polyurethane processing equipment. This is potentially of a great advantage in so far that it permits foam processing with various types of systems and equipment, including: masterbatch type blending equipment, gaseous blowing agent blending equipment, third stream addition of the blowing agent, or blowing agent addition at the foam head.

Example 5—Polyurethane Foam K-Factors

This example further demonstrates the unexpected performance of blowing agents in accordance with the present invention as used in the production of polyurethane foams. Three appliance polyurethane foams are made, each one being formed using substantially the same materials, procedures and equipment, with the exception that different blowing agents are used. The polyol system is a commercially available, appliance-type formulation adapted for use with a liquid blowing agent. A foam machine is used to form the foam. The blowing agents are used in essentially equal molar concentrations. After formation, each foam is cut into samples suitable for measuring k-factors, which are found to be as indicated in the following Table 5B below. The blowing agent composition in weight percent on the basis of total blowing agent is disclosed in Table 5A below:

TABLE 5A

| Blowing Agent | A | B | C |
|---|---|---|---|
| HFO-1234ze* | 85 | 0 | 60 |
| HFC-245fa | 15 | 100 | 11 |
| Cyclopentane | 0 | 0 | 29 |

*100% cis

TABLE 5B

| Mean Temperature | k-factor (BTU in/hr ft² ° F.) | | |
|---|---|---|---|
| (° F.) | A | B | C |
| 40 | 0.116 | 0.119 | 0.116 |
| 75 | 0.131 | 0.134 | 0.132 |
| 110 | 0.146 | 0.149 | 0.148 |

The results reported in Table 8C illustrate that the use of a compound of the present invention (HFO-1234ze) in combination with cyclopentane and HFC-245fa as co-blowing agents for thermoset foams at these levels did not impact in a deleterious manner the k-factor performance of HFO-1234ze when used alone or with HFC-245fa. This is an unexpected result because hereto for the use of cyclopentane in substantial amounts in blowing agent formulations has had a deleterious impact on k-factor performance.

Example 6—Polyurethane Foam K-Factors

A further experiment was performed using the same polyol formulation and isocyanate as in Example 5. The foam is prepared by hand mix, The blowing agents consist of a compound in accordance with Formula II, namely, HFCO-1233zd (CF$_3$CH=CHCl)* in about the same mole percentage of the foamable composition as the blowing agent in Example 5. K-factors are found to be as indicated in Table 6 below.

TABLE 6

| Mean Temperature (° F.) | k-factor (BTU in/ hr ft$^2$ ° F.) |
|---|---|
| 40 | 0.127 |
| 75 | 0.143 |
| 110 | 0.159 |

What is claimed is:

1. A method of forming an integral skin thermoset foam comprising:
   providing a thermosetting polymer foam formulation comprising a blowing agent composition comprising from about 5% by weight to about 95% by weight of a C4 fluoroalkene according to the following formula:

XCF$_3$ where X is a C3 unsaturated, substituted radical having at least one fluorine substituent; and
   foaming said polymer foam formulation to form a thermoset integral skin foam having improved compressive strength compared to a foam produced under substantially identical conditions by utilizing a blowing agent consisting of cyclopentane.

2. The method of claim 1 wherein said foam comprises a polyurethane foam.

3. The method of claim 1 wherein said blowing agent further comprises a hydrofluorocarbon selected from the group consisting of difluoromethane (HFC32); 1,1,1,2,1-pentafluoroethane (HFC125); 1,1,1-trifluoroethane (HFC143a); 1,1,2,2tetrafluorothane (HFC134); 1,1,1,2-tetrafluoroethane (HFC134a); 1, I-difluoroethane (HFC152a); 1,1,1,2,3,3,3-heptafluoropropane (HFC227ea); 1,1,1,3,3pentatfluoropropane (HFC245fa); 1,1,1,3,3-pentafluorobutane (HFC365mfc).

4. The method of claim 1 wherein said blowing agent further comprises 1,1,1,2,2,3,4,5,5,5-decafluoropentane (HFC4310mee).

5. The method of claim 1 wherein said blowing agent further comprises an additive selected from the group consisting of hydrocarbons, C1 to C5 alcohols, C1 to C4 aldehydes, C1 to C4 ketones, C1 to C4 ethers, carbon dioxide, and C1 to C4 diethers.

6. The method of claim 5 wherein said hydrocarbon is selected from the group consisting of pentane isomers and butane isomers.

7. A process of foaming a thermoset polyurethane integral skin foam comprising:
   (a) mixing polymer foam components capable of forming an integral skin foam with a foam blowing agent comprising a C4 fluoroalkene according to the following formula:

XCF$_3$ where X is a C3 unsaturated, substituted radical having at least one fluorine substituent; and
   (b) forming an integral skin thermoset polyurethane foam from said polymer foam components.

8. A process of foaming thermoset polyurethane integral skin foam comprising:
   (a) mixing polymer foam components capable of forming an integral skin foam with at least one C4 HFO having at least one —CF3 terminal group; and
   (b) forming an integral skin thermoset polyurethane foam from said polymer foam components.

9. The method of claim 8 wherein said C4 HFO comprises a hexafluorobutene.

* * * * *